(12) United States Patent
Kubo

(10) Patent No.: US 11,089,943 B2
(45) Date of Patent: Aug. 17, 2021

(54) ENDOSCOPE SYSTEM AND METHOD OF OPERATING THE SAME

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/871,823

(22) Filed: May 11, 2020

(65) Prior Publication Data

US 2020/0268231 A1 Aug. 27, 2020

Related U.S. Application Data

(63) Continuation of application No. PCT/JP2018/041289, filed on Nov. 7, 2018.

(30) Foreign Application Priority Data

Nov. 13, 2017 (JP) .............................. JP2017-217890

(51) Int. Cl.
*A61B 1/06* (2006.01)
*A61B 1/00* (2006.01)
(Continued)

(52) U.S. Cl.
CPC ........ *A61B 1/0005* (2013.01); *A61B 1/00006* (2013.01); *A61B 1/00188* (2013.01);
(Continued)

(58) Field of Classification Search
CPC ......... H04N 5/2352; H04N 2005/2255; H04N 5/23245; H04N 5/2354; H04N 5/2256;
(Continued)

(56) References Cited

U.S. PATENT DOCUMENTS 9,851,303 B2 * 12/2017 Huber .................. G01J 3/4406
2009/0023991 A1 1/2009 Gono et al.
(Continued)

FOREIGN PATENT DOCUMENTS

JP 2005204905 A 8/2005
JP 2006-341078 A 12/2006
(Continued)

OTHER PUBLICATIONS

International Search Report issued in PCT/JP2018/041289; dated Jan. 29, 2019.
(Continued)

*Primary Examiner* — Howard D Brown, Jr.
(74) *Attorney, Agent, or Firm* — Studebaker & Brackett PC

(57) ABSTRACT

In a mono-light emission mode, specific illumination light is emitted and a specific observation image obtained from the image pickup of an object to be observed illuminated with the specific illumination light is displayed on a monitor 18. In a multi-light emission mode, first illumination light and second illumination light are emitted while being switched according to a specific light emission pattern and a first observation image and a second observation image are displayed on the monitor 18 while being switched according to a specific display pattern. In a case where a designated condition set in advance by a user is satisfied, a mode is automatically switched to the mono-light emission mode from the multi-light emission mode.

12 Claims, 13 Drawing Sheets

(51) Int. Cl.
*A61B 1/04* (2006.01)
*A61B 1/273* (2006.01)
*H04N 5/235* (2006.01)
*H04N 5/225* (2006.01)

(52) U.S. Cl.
CPC .............. *A61B 1/04* (2013.01); *A61B 1/0638* (2013.01); *A61B 1/0646* (2013.01); *A61B 1/0661* (2013.01); *A61B 1/0684* (2013.01); *A61B 1/273* (2013.01); *H04N 5/2352* (2013.01); *H04N 2005/2255* (2013.01)

(58) Field of Classification Search
CPC .......... H04N 9/64; G02B 23/26; G02B 23/24; A61B 1/0005; A61B 1/00006; A61B 1/00188; A61B 1/04; A61B 1/0638; A61B 1/0646; A61B 1/0661; A61B 1/0684; A61B 1/273; A61B 1/045; A61B 1/00009
See application file for complete search history.

(56) References Cited

U.S. PATENT DOCUMENTS

| | | | |
|---|---|---|---|
| 2011/0230712 A1 | 9/2011 | Matsuura et al. | |
| 2012/0253158 A1 | 10/2012 | Yamaguchi et al. | |
| 2013/0018242 A1* | 1/2013 | Yamaguchi | A61B 5/14551 600/339 |
| 2013/0041218 A1* | 2/2013 | Iida | A61B 1/00006 600/109 |
| 2014/0316195 A1 | 10/2014 | Kaku et al. | |
| 2014/0371527 A1 | 12/2014 | Sato | |
| 2019/0038111 A1 | 2/2019 | Endo | |

FOREIGN PATENT DOCUMENTS

| | | | |
|---|---|---|---|
| JP | 2007-020728 | A | 2/2007 |
| JP | 2010-046354 | A | 3/2010 |
| JP | 2012-000160 | A | 1/2012 |
| JP | 2012213551 | A | 11/2012 |
| JP | 2013-017769 | A | 1/2013 |
| JP | 2013-034753 | A | 2/2013 |
| JP | 2013-150712 | A | 8/2013 |
| JP | 2013252356 | A | 12/2013 |
| JP | 2014-076375 | A | 5/2014 |
| JP | 2015-000093 | A | 1/2015 |
| JP | 2016-007336 | A | 1/2016 |
| JP | 2017-192565 | A | 10/2017 |
| JP | 2017192501 | A | 10/2017 |
| WO | 2006/120798 | A1 | 11/2006 |
| WO | 2011/016428 | A1 | 2/2011 |

OTHER PUBLICATIONS

International Preliminary Report on Patentability and Written Opinion issued in PCT/JP2018/041289; dated May 19, 2020.
An Office Action; "Notice of Reasons for Refusal," mailed by the Japanese Patent Office dated Nov. 4, 2020, which corresponds to Japanese Patent Application No. 2019-552831 and is related to U.S. Appl. No. 16/871,823; with English language translation.

* cited by examiner

ENDOSCOPE SYSTEM AND METHOD OF OPERATING THE SAME

CROSS-REFERENCE TO RELATED APPLICATIONS

This application is a Continuation of PCT International Application No. PCT/JP2018/041289 filed on 7 Nov. 2018, which claims priority under 35 U.S.C § 119(a) to Japanese Patent Application No. 2017-217890 filed on 13 Nov. 2017. The above application is hereby expressly incorporated by reference, in its entirety, into the present application.

BACKGROUND OF THE INVENTION

1. Field of the Invention

The present invention relates to an endoscope system and a method of operating the endoscope system that illuminate an object with a plurality of kinds of illumination light having different wavelength ranges while switching the plurality of kinds of illumination light and display observation images corresponding to the plurality of kinds of illumination light while switching the observation images.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked by an image pickup element of the endoscope.

Further, in recent years, an object to be observed has been illuminated with a plurality of kinds of illumination light having different wavelength ranges to obtain much diagnosis information from the object to be observed. For example, JP2012-213551A (corresponding to US2012/0253158A1) discloses a device that illuminates an object to be observed with wavelength sets formed of narrow-band light having wavelengths of four hundreds nm, five hundreds nm, and six hundreds nm while automatically switching the narrow-band light to allow a user to observe the oxygen saturation of superficial blood vessels, the oxygen saturation of middle-layer blood vessels, and the oxygen saturation of deep blood vessels included in the object to be observed.

SUMMARY OF THE INVENTION

In a case where a user is to frequently confirm a plurality of observation images, an object to be observed is illuminated with a plurality of kinds of illumination light while the plurality of kinds of illumination light are automatically switched and observation images corresponding to the plurality of kinds of illumination light are displayed while being automatically switched. Accordingly, the user can confirm the respective observation images without a burden. However, in a case where the object to be observed is illuminated with the plurality of kinds of illumination light while the plurality of kinds of illumination light are switched as described above, the object to be observed is required to be reliably illuminated with each illumination light. For this reason, in a case where a distal end part of an endoscope, which emits illumination light and picks up the image of an object to be observed, is moved unintentionally or an object to be observed is out of focus and illumination light hardly reaches the object to be observed, illuminating an object to be observed with a plurality of kinds of illumination light while switching the plurality of kinds of illumination light may not be suitable.

An object of the invention is to provide an endoscope system and a method of operating the endoscope system that can appropriately cope with a situation not suitable for illuminating an object with a plurality of kinds of illumination light while switching the plurality of kinds of illumination light in a case where the object to be observed is to be illuminated with the plurality of kinds of illumination light while the plurality of kinds of illumination light are automatically switched and observation images corresponding to the plurality of kinds of illumination light are displayed while being switched.

An endoscope system according to an aspect of the invention comprises a plurality of semiconductor light sources, a light source control unit, a display control unit, and an automatic mode-switching unit. The plurality of semiconductor light sources emit light having wavelength ranges different from each other. The light source control unit controls the plurality of semiconductor light sources, and performs control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern. The display control unit performs control to display a specific observation image, which is obtained from image pickup of an object to be observed illuminated with the specific illumination light, on a display unit in the mono-light emission mode, and performs control to display a plurality of observation images, which include a first observation image obtained from image pickup of the object to be observed illuminated with the first illumination light and a second observation image obtained from image pickup of the object to be observed illuminated with the second illumination light, on the display unit while switching the plurality of observation images according to a specific display pattern in the multi-light emission mode. The automatic mode-switching unit automatically switches a mode to the mono-light emission mode from the multi-light emission mode in a case where a designated condition set in advance by a user is satisfied.

It is preferable that the designated condition is that a use time of the multi-light emission mode is equal to or longer than a time threshold value. It is preferable that the designated condition is that the number of times of storage of a static image of the object to be observed is equal to or larger than a number-of-times threshold value.

It is preferable that the designated condition is a case where an image pickup condition about the object to be observed is changed. It is preferable that the object to be observed includes a first site and a second site different from the first site and the designated condition is a case where the object to be observed is changed to the second site from the first site or a case where the object to be observed is changed to the first site from the second site. It is preferable that the first site is a gullet and the second site is a stomach. It is preferable that the designated condition is a case where brightness of the object to be observed is equal to or lower than a first brightness threshold value or is equal to or higher than a second brightness threshold value larger than the first brightness threshold value. It is preferable that the endoscope system further comprises a magnification change unit used to change magnification of the object to be observed, and the designated condition is a case where a variation of magnification of the object to be observed exceeds a magnification threshold value. It is preferable that the endoscope system further comprises an observation distance acquisition section acquiring an observation distance indicating a distance to the object to be observed, and the designated condition is a case where a variation of the observation distance exceeds a distance threshold value. It is preferable that the endoscope system further comprises a shake amount calculation section calculating a shake amount of the observation image, and the designated condition is a case where the shake amount exceeds a shake-amount threshold value.

A method of operating an endoscope system according to another aspect of the invention comprises a light source control step, a display control step, and a mode switching step. In the light source control step, a light source control unit, which controls a plurality of semiconductor light sources emitting light having wavelength ranges different from each other, performs control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern. In the display control step, a display control unit performs control to display a specific observation image, which is obtained from image pickup of an object to be observed illuminated with the specific illumination light, on a display unit in the mono-light emission mode and performs control to display a plurality of observation images, which include a first observation image obtained from image pickup of the object to be observed illuminated with the first illumination light and a second observation image obtained from image pickup of the object to be observed illuminated with the second illumination light, on the display unit while switching the plurality of observation images according to a specific display pattern in the multi-light emission mode. In the mode switching step, an automatic mode-switching unit automatically switches a mode to the mono-light emission mode from the multi-light emission mode in a case where a designated condition set in advance by a user is satisfied.

According to the invention, it is possible to appropriately cope with a situation not suitable for illuminating an object with a plurality of kinds of illumination light while switching the plurality of kinds of illumination light in a case where the object to be observed is to be illuminated with the plurality of kinds of illumination light while the plurality of kinds of illumination light are automatically switched and observation images corresponding to the plurality of kinds of illumination light are displayed while being switched.

DESCRIPTION OF THE PREFERRED EMBODIMENTS

Figure 1:
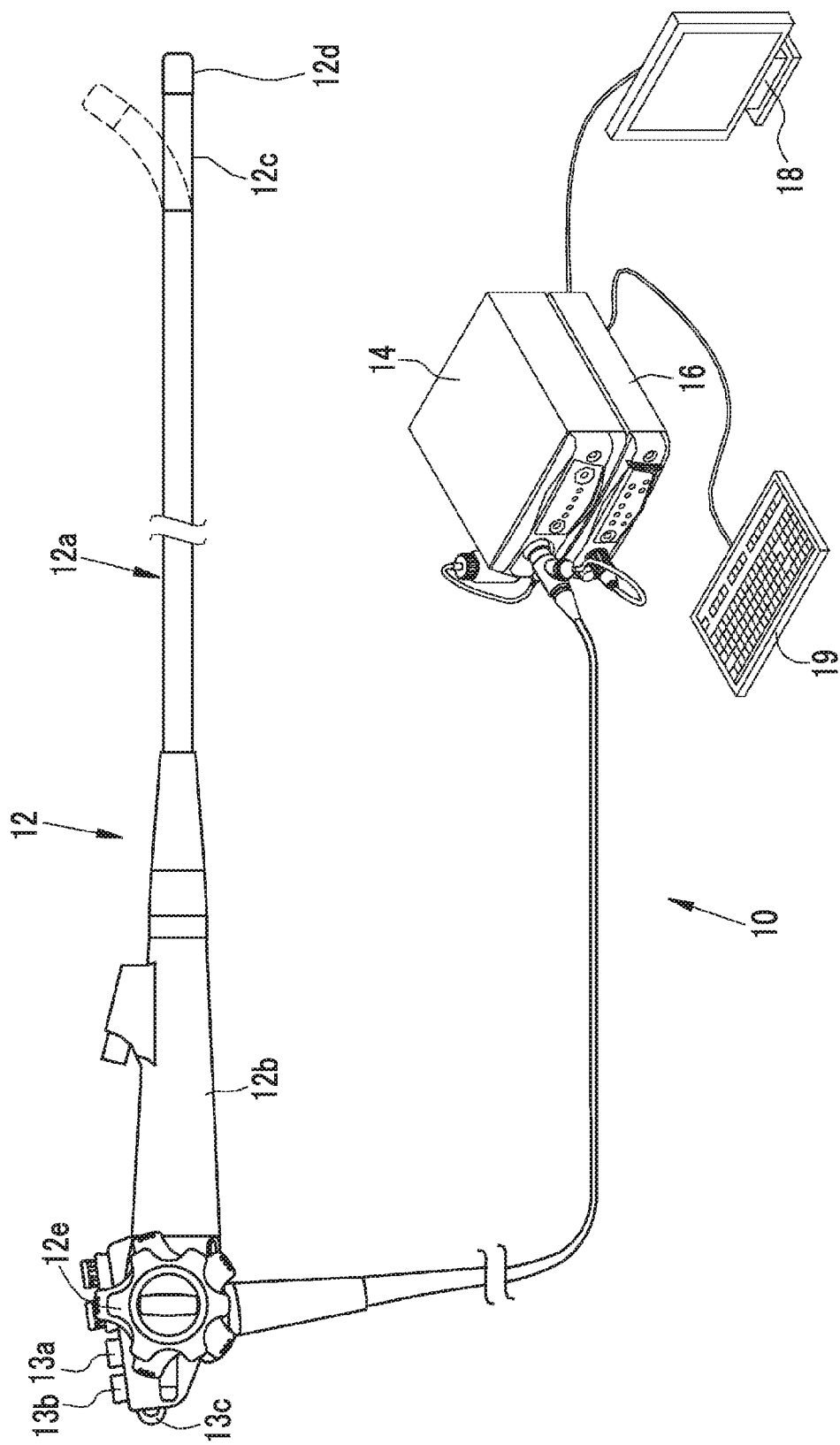
FIG. 1 is a diagram showing the appearance of an endoscope system according to a first embodiment.

As shown in FIG. 1, an endoscope system 10 includes an endoscope 12, a light source device 14, a processor device 16, a monitor 18, and a keyboard 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d faces in a desired direction. A mouse and the like are included in the keyboard 19 in addition to a keyboard (not shown).

Further, the operation part 12b is provided with a mode changeover SW 13a, a static-image-acquisition instruction part 13b, and a zoom operation part 13c in addition to the angle knobs 12e. The mode changeover SW 13a is used to switch a normal mode and a multi-light emission mode. In the normal mode, normal light (specific illumination light) is emitted and a normal image (specific observation image) is displayed on the monitor 18. In the multi-light emission mode, first illumination light for emphasizing superficial blood vessels and second illumination light for emphasizing deep blood vessels are emitted while being switched according to a specific light emission pattern. Further, in the multi-light emission mode, a first observation image, which is obtained in a case where an object to be observed is illuminated with the first illumination light, and a second observation image, which is obtained in a case where the object to be observed is illuminated with the second illumination light, are displayed on the monitor 18 while being switched according to a specific display pattern. A "mono-light emission mode" of the invention corresponds to the normal mode.

The static-image-acquisition instruction part 13b is used to instruct a static image-storage unit 63 (see FIG. 2) to store the static image of the object to be observed. The zoom operation part 13c is used to operate a zoom lens 47 and a zoom drive unit 47a (see FIG. 2) that are provided in the endoscope 12.

The processor device 16 is electrically connected to the monitor 18 and the keyboard 19. The monitor 18 outputs and displays image information and the like. The keyboard 19 functions as a user interface (UI) that receives an input operation, such as function settings. An external recording unit (not shown), which records image information and the like, may be connected to the processor device 16.

Figure 2:
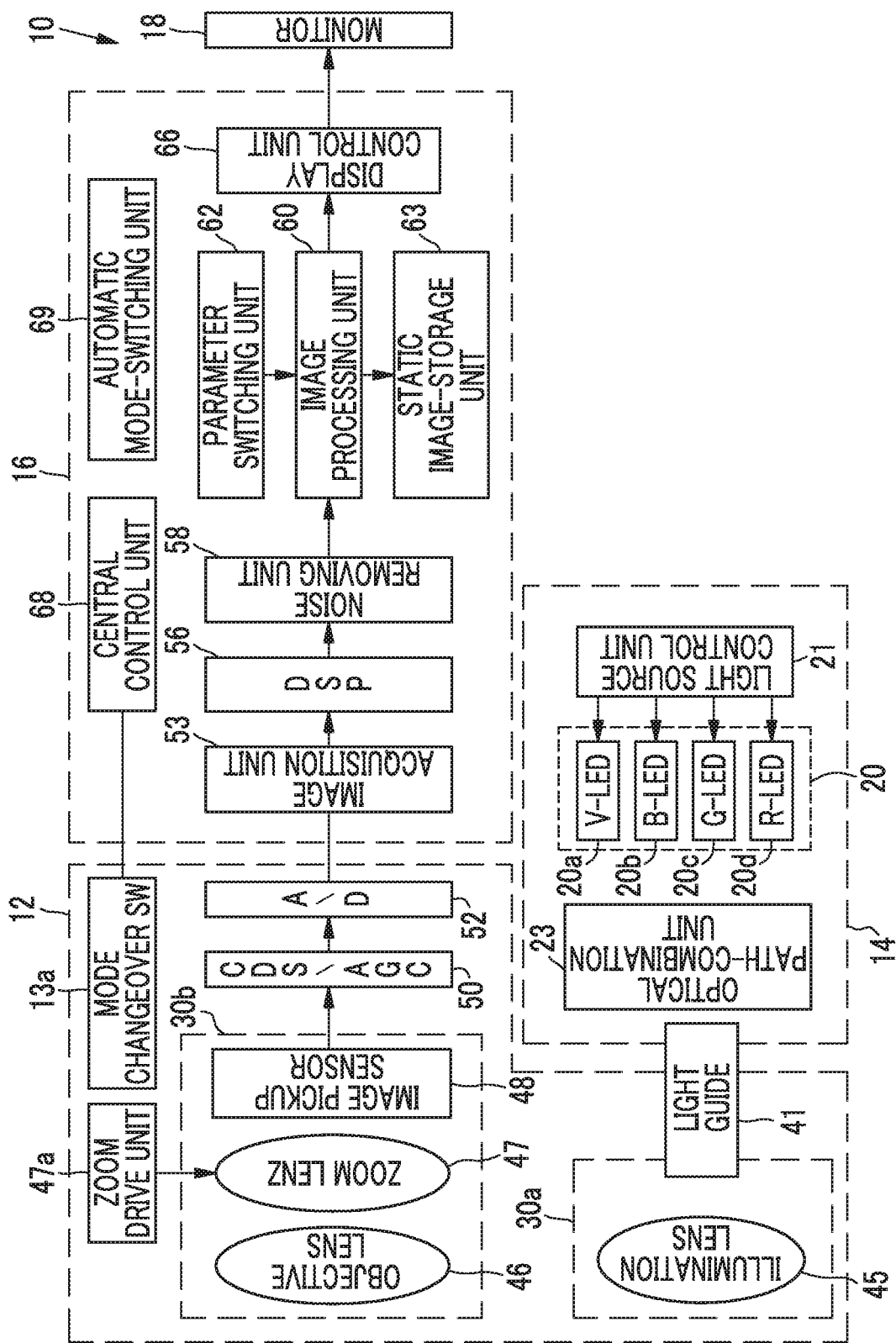
FIG. 2 is a block diagram showing the functions of the endoscope system according to the first embodiment.

As shown in FIG. 2, the light source device 14 includes a light source unit 20, a light source control unit 21, and an optical path-combination unit 23. The light source unit 20 can emit light having a plurality of wavelength ranges, and can change the light emission ratio of the light having each wavelength range. In this specification, "light having a plurality of wavelength ranges different from each other" means that the plurality of wavelength ranges may partially overlap with each other without meaning that the plurality of wavelength ranges do not overlap with each other at all. The light source unit 20 includes a violet light emitting diode (V-LED) 20a, a blue light emitting diode (B-LED) 20b, a green light emitting diode (G-LED) 20c, and a red light emitting diode (R-LED) 20d to emit light having a plurality of wavelength ranges. Since it is preferable that the light source unit 20 is provided with a plurality of semiconductor light sources, a laser diode (LD) may be used instead of the LED.

The light source control unit 21 controls the drive of the LEDs 20a to 20d. The optical path-combination unit 23 combines the optical paths of pieces of light that are emitted from the four color LEDs 20a to 20d and have four colors.

The inside of an object to be examined is irradiated with the pieces of light, which are combined by the optical path-combination unit 23, through a light guide 41 inserted into the insertion part 12a and an illumination lens 45.

Figure 3:
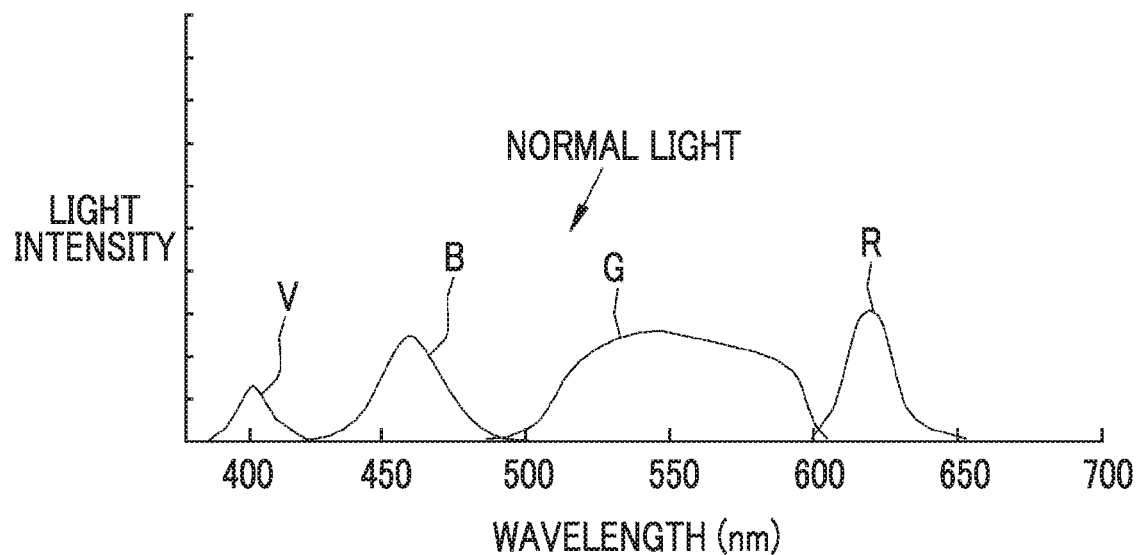
FIG. 3 is a graph showing the emission spectra of violet light V, blue light B, green light G, and red light R.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm.

Figure 4:
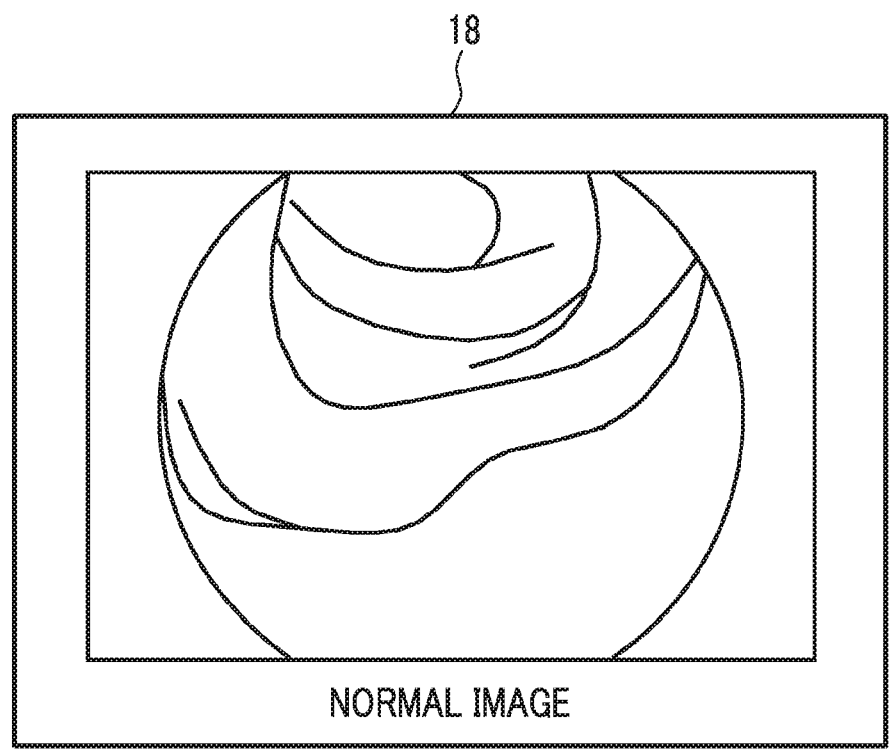
FIG. 4 is an image diagram showing a normal image.

The light source control unit 21 performs control to turn on the V-LED 20a, the B-LED 20b, the G-LED 20c, and the R-LED 20d in all modes. Further, the light source control unit 21 controls the respective LEDs 20a to 20d so that normal light of which the light intensity ratios of violet light V, blue light B, green light G, and red light R are Vc:Bc:Gc:Rc is emitted in the normal mode (see FIG. 3). In a case where the image of the object to be observed illuminated with this normal light is picked up, the normal image where superficial blood vessels are emphasized as shown in FIG. 4 is obtained. In this specification, a light emission ratio means the light intensity ratio of each semiconductor light source and includes a case where the light intensity ratio is 0 (zero). Accordingly, the light emission ratio includes a case where any one or two of the respective semiconductor light sources are not turned on. For example, even in a case where only one semiconductor light source is turned on and the other three semiconductor light sources are not turned on as in a case where the light intensity ratios of violet light V, blue light B, green light G, and red light R are 1:0:0:0, it is considered that the light source unit has a light emission ratio.

Figure 5:
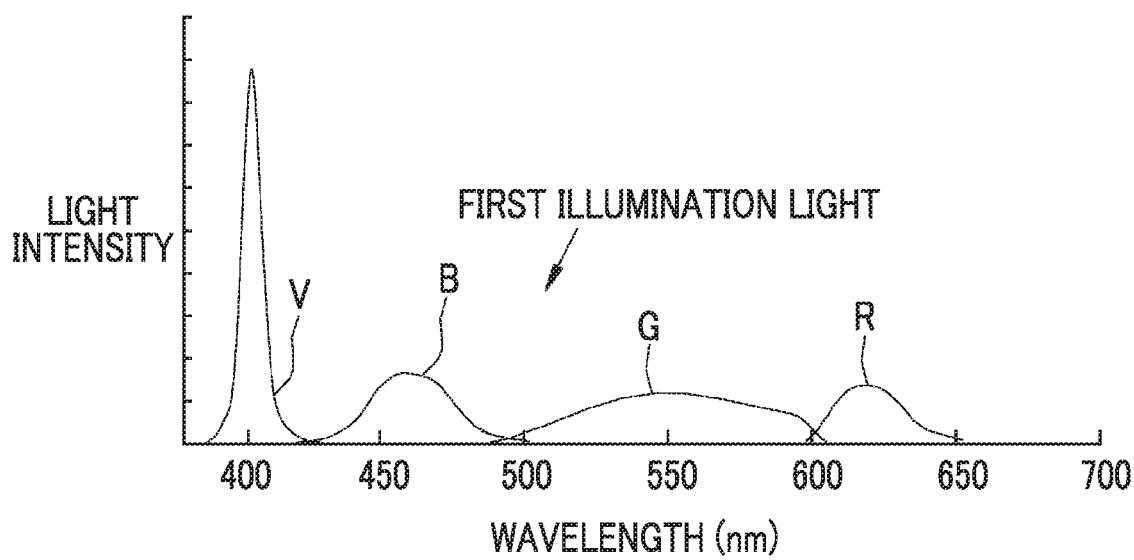
FIG. 5 is a graph showing the emission spectrum of first illumination light that includes violet light V, blue light B, green light G, and red light R.
Figure 6:
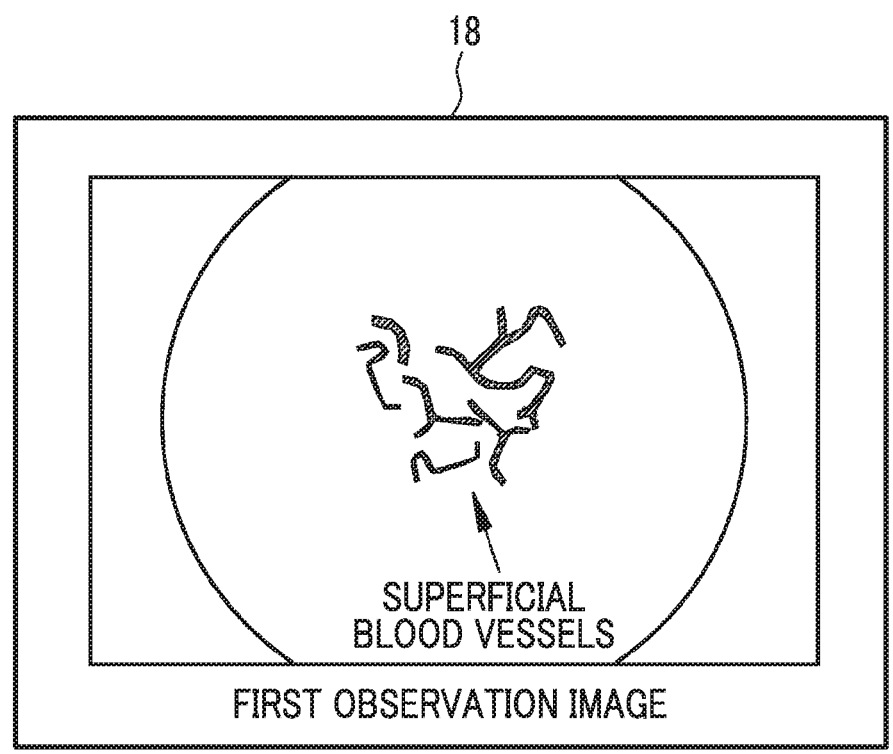
FIG. 6 is an image diagram showing a first observation image.

Furthermore, the light source control unit 21 controls the respective LEDs 20a to 20d so that the first illumination light to be emitted in the multi-light emission mode is emitted to have the light emission ratios of violet light V, blue light B, green light G, and red light R of Vs1:Bs1:Gs1:Rs1. It is preferable that the first illumination light has a peak in the range of 400 nm to 440 nm. For this purpose, Vs1:Bs1:Gs1:Rs1 of the first illumination light are set so that the light intensity of violet light V is higher than the light intensity of each of blue light B, green light G, and red light R as shown in FIG. 5 (Vs1>Bs1, Gs1, and Rs1). In a case where the image of the object to be observed illuminated with the first illumination light is picked up, the first observation image where superficial blood vessels are emphasized as shown in FIG. 6 is obtained.

Further, since the first illumination light includes a first red-light wavelength range like red light R, the first illumination light can accurately reproduce the color of a mucous membrane. Furthermore, since the first illumination light includes a first blue-light wavelength range and a first green-light wavelength range like violet light V, blue light B, and green light G, the first illumination light can also emphasize various structures, such as glandular structures and unevenness, in addition to the above-mentioned superficial blood vessels.

Furthermore, the light source control unit 21 controls the respective LEDs 20a to 20d so that the second illumination light to be emitted in the multi-light emission mode is emitted to have the light emission ratios of violet light V, blue light B, green light G, and red light R of Vs2:Bs2:Gs2:

Rs2. It is preferable that the intensity ratio of the second illumination light is higher than that of the first illumination light at wavelengths of 460 nm, 540 nm, and 630 nm.

Figure 7:
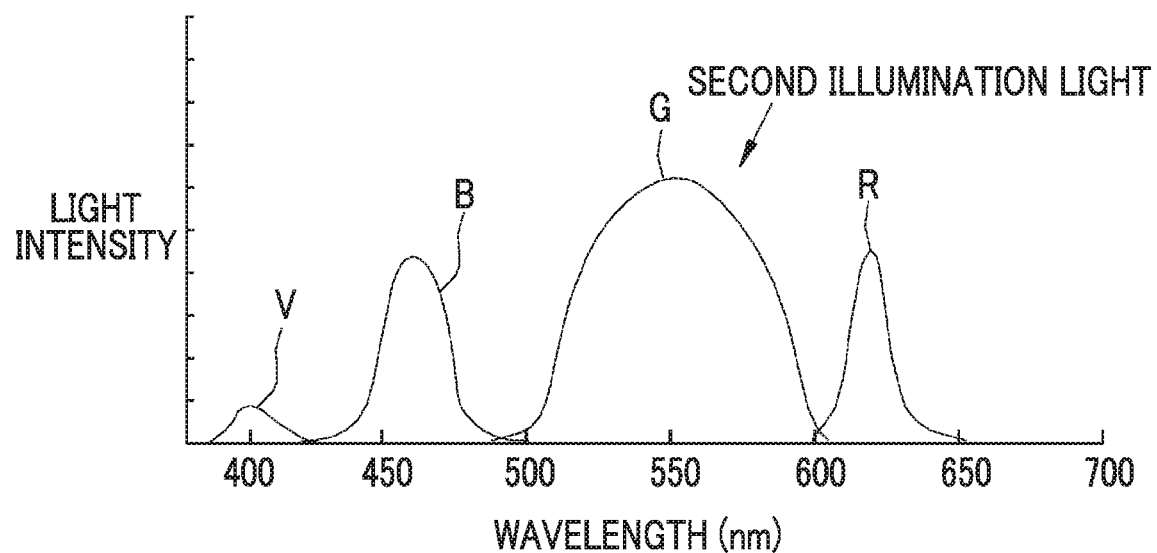
FIG. 7 is a graph showing the emission spectrum of second illumination light that includes violet light V, blue light B, green light G, and red light R.
Figure 8:
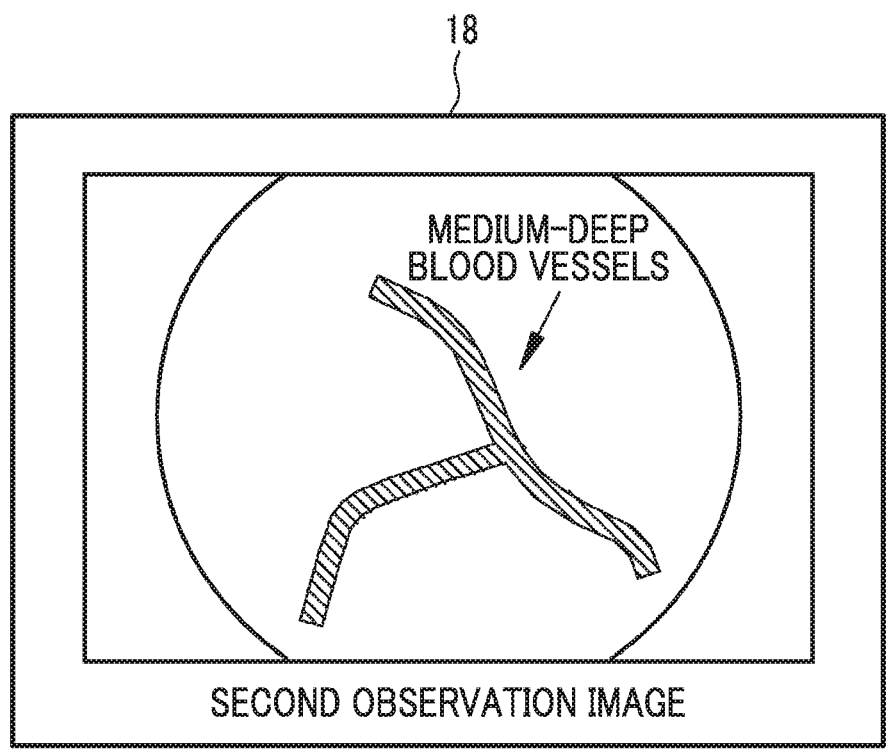
FIG. 8 is an image diagram showing a second observation image.

For this purpose, Vs2:Bs2:Gs2:Rs2 of the second illumination light are set so that the amounts of blue light B, green light G, and red light R of the second illumination light are larger than the amounts of blue light B, green light G, and red light R of the first illumination light as shown in FIG. 7. In a case where the image of an object to be observed illuminated with the second illumination light is picked up, a second observation image where medium-deep blood vessels are emphasized as shown in FIG. 8 is obtained.

Vs2:Bs2:Gs2:Rs2 are set so that the light intensity of violet light V is lower than the light intensity of each of blue light B, green light G, and red light R (Vs2<Bs2, Gs2, and Rs2). Further, since the second illumination light includes a second red-light wavelength range like red light R, the second illumination light can accurately reproduce the color of a mucous membrane. Furthermore, since the second illumination light includes a second blue-light wavelength range and a second green-light wavelength range like violet light V, blue light B, and green light G, the second illumination light can also emphasize various structures, such as glandular structures and unevenness, in addition to the above-mentioned medium-deep blood vessels.

Figure 9:
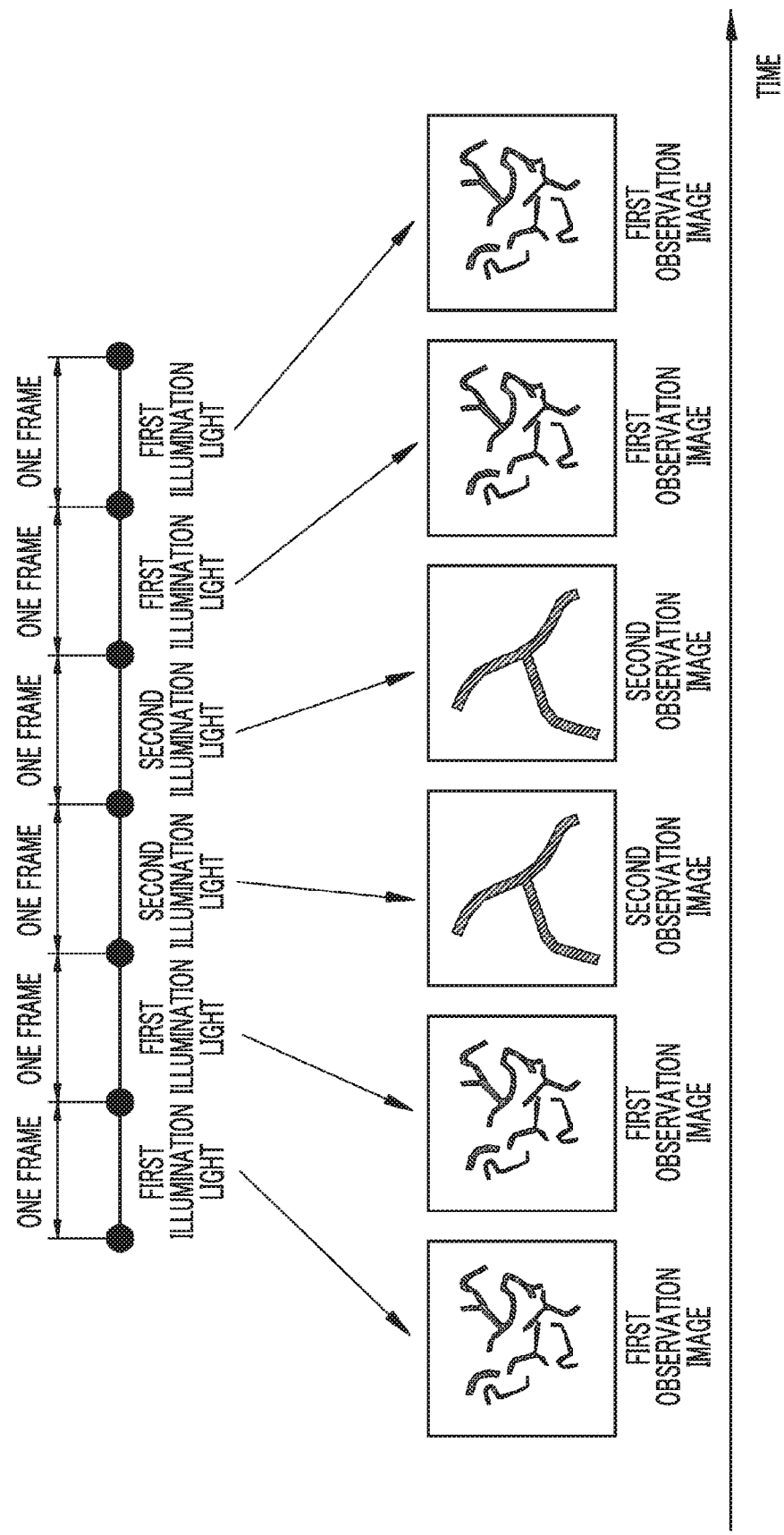
FIG. 9 is a diagram showing the light emission of the first illumination light and the second illumination light and the display of the first and second observation images in a multi-light emission mode.

Further, in a case where a mode is set to the multi-light emission mode, the light source control unit 21 performs control to emit the first illumination light and the second illumination light while automatically switching the first illumination light and the second illumination light according to the specific light emission pattern. In this embodiment, as the specific light emission pattern, the first illumination light and the second illumination light are emitted while being switched at an interval of two frames as shown in FIG. 9. Further, as the specific display pattern, the first observation image obtained using the light emission of the first illumination light and the second observation image obtained using the light emission of the second illumination light are displayed on the monitor 18 while being switched at an interval of two frames.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of φ0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46, a zoom lens 47, and an image pickup sensor 48. Light reflected from the object to be observed is incident on the image pickup sensor 48 through the objective lens 46 and the zoom lens 47. Accordingly, the reflected image of the object to be observed is formed on the image pickup sensor 48. The zoom lens 47 can be moved along an optical axis by the zoom drive unit 47a. The size of the image of the object to be observed is increased or reduced due to the movement of the zoom lens 47. A "magnification change unit" of the invention corresponds to configuration that includes the zoom operation part 13c, the zoom lens 47, and the zoom drive unit 47a.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-filters, G-pixels provided with G-filters, and B-pixels provided with B-filters.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 corresponds to a medical image processing device that processes medical images, such as images obtained by the endoscope 12. The processor device 16 comprises an image acquisition unit 53, a digital signal processor (DSP) 56, a noise removing unit 58, an image processing unit 60, a parameter switching unit 62, a display control unit 66, a central control unit 68, and an automatic mode-switching unit 69. Digital color image signals output from the endoscope 12 are input to the image acquisition unit 53. The color image signals are RGB image signals formed of R-image signals that are output from the R-pixels of the image pickup sensor 48, G-image signals that are output from the G-pixels of the image pickup sensor 48, and B-image signals that are output from the B-pixels of the image pickup sensor 48.

The DSP 56 performs various kinds of signal processing, such as defect correction processing, offset processing, gain processing, color adjustment processing, gamma conversion processing, and demosaicing processing, on the received image signals. Signals of defective pixels of the image pickup sensor 48 are corrected in the defect correction processing. Dark current components are removed from the RGB image signals having been subjected to the defect correction processing in the offset processing, so that an accurate zero level is set.

The RGB image signals having been subjected to the offset processing are multiplied by a specific gain parameter in the gain processing, so that signal levels are adjusted. The specific gain parameter varies for each mode. For example, gain processing for normal light for multiplying image signals, which are obtained from the illumination of the normal light and image pickup, by a gain parameter for normal light as the specific gain parameter is performed in the normal mode. Further, in the multi-light emission mode, gain processing for first illumination light for multiplying RGB image signals, which are obtained from the illumination of the first illumination light and image pickup, by a gain parameter for first illumination light as the specific gain parameter is performed at the time of the illumination of the first illumination light, and gain processing for second illumination light for multiplying RGB image signals, which are obtained from the illumination of the second illumination light and image pickup, by a gain parameter for second illumination light as the specific gain parameter is performed at the time of the illumination of the second illumination light.

After that, brightness or a saturation is adjusted by the gamma conversion processing. The demosaicing processing (also referred to as equalization processing or demosaicing) is performed on the RGB image signals having been subjected to the linear matrix processing, so that signals of colors deficient in each pixel are generated by interpolation. All the pixels are made to have the signals of the respective colors of R, G, and B by this demosaicing processing.

The noise removing unit 58 performs noise removal processing (for example, a moving-average method, a median filtering method, or the like) on the RGB image signals, which have been subjected to gamma correction and the like by the DSP 56, to remove noise from the RGB image signals. The RGB image signals from which noise has been removed are transmitted to the image processing unit 60.

The image processing unit 60 performs various kinds of image processing on the RGB image signals. The various kinds of image processing include image processing that is performed under a condition varying for each mode in addition to image processing that is performed under the same condition regardless of the normal mode or the multi-light emission mode. The image processing that is performed under a condition varying for each mode includes color adjustment processing for improving color reproducibility and structure emphasis processing for emphasizing various structures, such as blood vessels and unevenness. Each of the color adjustment processing and the structure emphasis processing is processing that uses a two-dimensional look up table (LUT), a three-dimensional look up table (LUT), a matrix, or the like. In a case where the color emphasis processing and the structure emphasis processing are to be performed, a color emphasis processing parameter and a structure emphasis processing parameter set for each mode are used in the image processing unit 60. The switching of the color emphasis processing parameter or the structure emphasis processing parameter is performed by the parameter switching unit 62.

In a case where a mode is set to the normal mode, a parameter to be used in the image processing unit 60 is switched to a color emphasis processing parameter for normal light and a structure emphasis processing parameter for normal light by the parameter switching unit 62. Then, the image processing unit 60 performs color emphasis processing for normal light on the RGB image signals using the color emphasis processing parameter for normal light, and performs structure emphasis processing for normal light on the RGB image signals using the structure emphasis processing parameter for normal light. After that, the RGB image signals having been subjected to the above-mentioned processing are input to the display control unit 66 as the normal image.

In a case where a mode is set to the multi-light emission mode, the image processing unit 60 performs color emphasis processing for first illumination light and structure emphasis processing for first illumination light on the RGB image signals at the time of the illumination of the first illumination light. After that, the RGB image signals having been subjected to the above-mentioned processing are input to the display control unit 66 as the first observation image. Further, the image processing unit 60 performs the color emphasis processing for second illumination light and the structure emphasis processing for second illumination light on the RGB image signals at the time of the illumination of the second illumination light. Furthermore, in a case where a mode is set to the multi-light emission mode, the image processing unit 60 performs mucous membrane-color-balance processing for setting the colors of normal mucous membranes, which are included in the object to be observed, to the same color between the first observation image and the second observation image. First mucous membrane-color-balance processing is performed on the first observation image, and second mucous membrane-color-balance processing based on the result of the first mucous membrane-color-balance processing is performed on the second observation image. After that, the RGB image signals having been subjected to the above-mentioned processing are input to the display control unit 66 as the second observation image.

B1-image signals, G1-image signals, and R1-image signals included in the first observation image are automatically adjusted in the first mucous membrane-color-balance processing as described in, for example, D1) to D3) to be described below so that the average color of the entire screen has a specific color balance. The first mucous membrane-color-balance processing is performed on the assumption that the color of a mucous membrane is dominant over the object to be observed. Then, the first mucous membrane-color-balance processing is performed, so that B1*-image signals, G1*-image signals, and R1*-image signals having been subjected to the first mucous membrane-color-balance processing are obtained.

D1) B1*-image signal=B1/B1ave
D2) G1*-image signal=G1/G1ave
D3) R1*-image signal=R1/R1ave Here, B1ave denotes the average pixel value of the B1-image signals (the sum of pixel values of the entire screen (effective pixels)/the number of effective pixels). G1ave denotes the average pixel value of the G1-image signals (the sum of pixel values of the entire screen (effective pixels)/the number of effective pixels). R1ave denotes the average pixel value of the R1-image signals (the sum of pixel values of the entire screen (effective pixels)/the number of effective pixels).

Further, B2-image signals, G2-image signals, and R2-image signals included in the second observation image are automatically adjusted in the second mucous membrane-color-balance processing as described in, for example, E1) to E3) to be described below so that the average color of the entire screen has a specific color balance. B1ave, G1 ave, and R1ave calculated in the first mucous membrane-color-balance processing are used in the second mucous membrane-color-balance processing. Then, the second mucous membrane-color-balance processing is performed, so that B2*-image signals, G2*-image signals, and R2*-image signals having been subjected to the second mucous membrane-color-balance processing are obtained.

E1) B2*image signal=B2/B1ave
E2) G2*image signal=G2/G1ave
E3) R2*image signal=R2/R1ave The display control unit 66 performs control to display the normal image, the first observation image, or the second observation image, which is input from the image processing unit 60, as an image that can be displayed on the monitor 18. In the normal mode, the display control unit 66 displays the normal image on the monitor 18. In the multi-light emission mode, the display control unit 66 displays the first observation image or the second observation image on the monitor 18 while switching the first and second observation images according to a specific display pattern (in this embodiment, "at an interval of two frames". See FIG. 9).

The central control unit 68 controls the respective parts of the processor device 16. Further, the central control unit 68 receives information from the endoscope 12 or the light source device 14, and performs the control of the respective parts of the processor device 16 and the control of the endoscope 12 or the light source device 14 on the basis of the received information.

Figure 10:
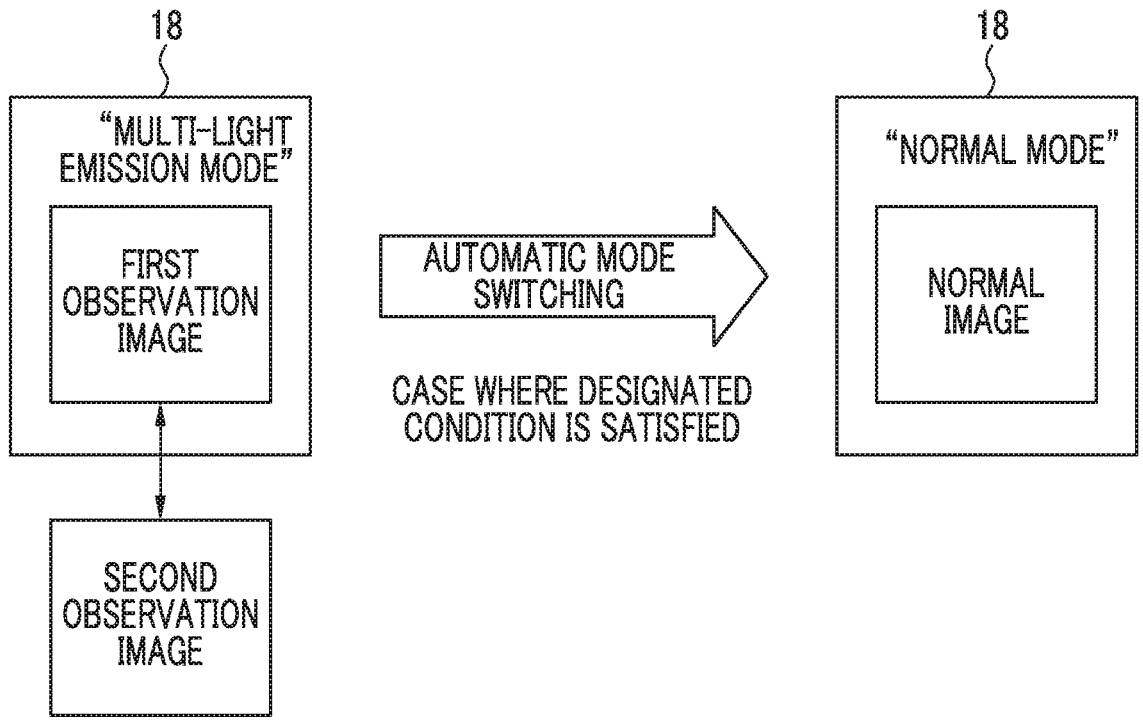
FIG. 10 is a diagram showing that a mode is automatically switched to a normal mode from the multi-light emission mode.

In a case where a mode is set to the multi-light emission mode and a designated condition set in advance by a user is satisfied, as shown in FIG. 10, the automatic mode-switching unit 69 performs processing for switching a mode to the normal mode where only the normal image continues to be displayed on the monitor 18 from the multi-light emission mode where the first observation image and the second observation image are displayed on the monitor 18 while being switched. The reason why a mode is to be capable of being automatically switched is that a user forget to switch a mode in a case where the object to be observed is not changed or is hardly changed. Since there is a case where it is difficult for a user to know to which one of the multi-light emission mode and the normal mode a mode is set, the monitor 18 displays that a mode is set to the "multi-light emission mode" in the multi-light emission mode and displays that a mode is set to the "normal mode" in the normal mode.

Figure 11:
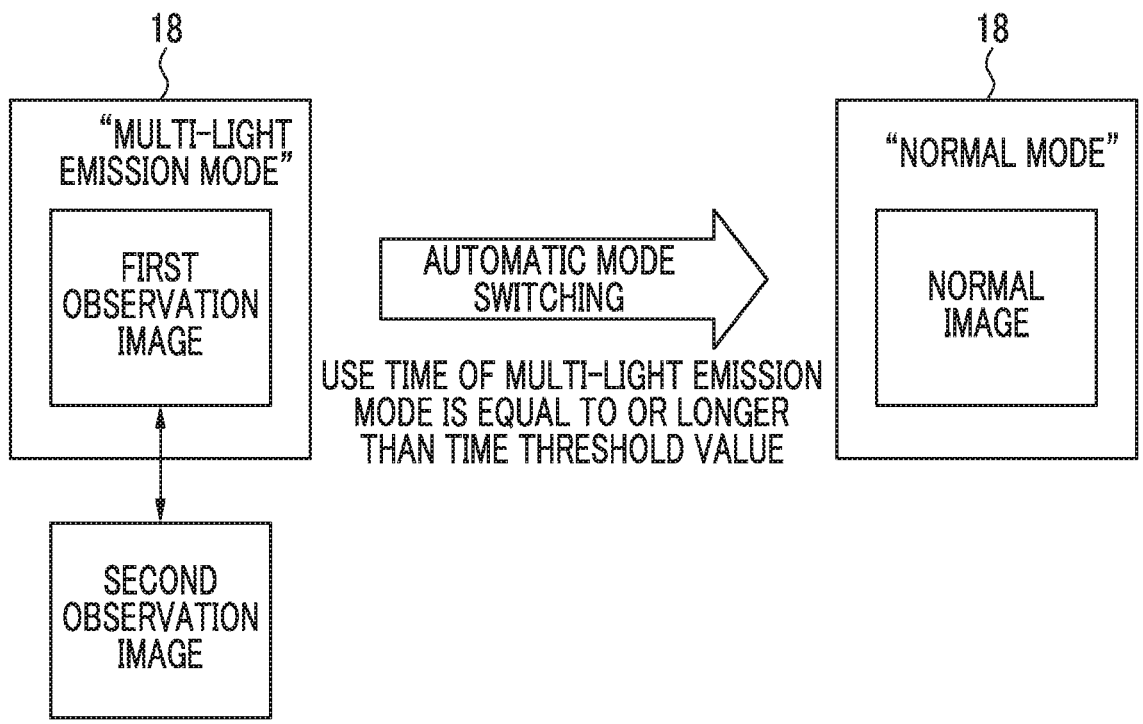
FIG. 11 is a diagram showing that a mode is automatically switched to the normal mode from the multi-light emission mode in a case where the use time of the multi-light emission mode is equal to or longer than a time threshold value.

The designated condition, which is used to switch a mode to the normal mode form the multi-light emission mode, is that, for example, the use time of the multi-light emission mode is equal to or longer than a predetermined time threshold value. In this case, a time, which has passed after a mode is set to the multi-light emission mode by the mode changeover SW 13*a*, is measured by a time measurement unit (not shown) provided in the processor device 16. Then, in a case where the measured time is equal to or longer than the time threshold value, a mode is automatically switched to the normal mode from the multi-light emission mode as shown in FIG. 11.

Figure 12:
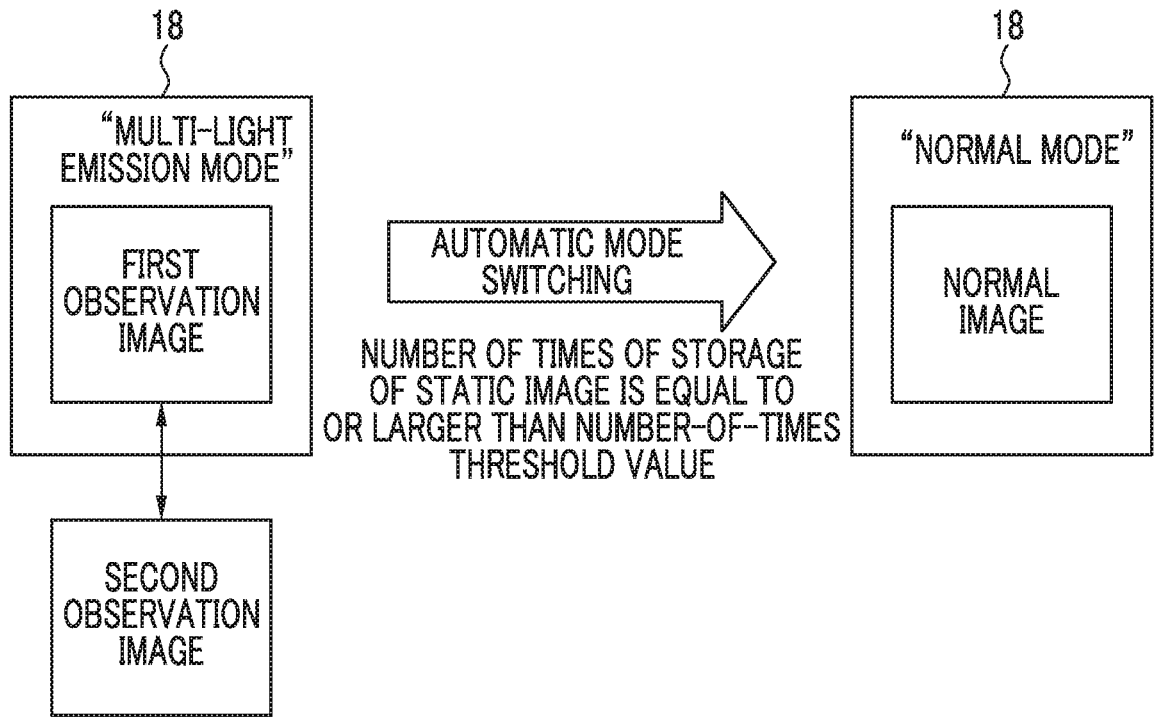
FIG. 12 is a diagram showing that a mode is automatically switched to the normal mode from the multi-light emission mode in a case where the number of times of storage of a static image is equal to or larger than a number-of-times threshold value.

Further, the designated condition is that, for example, the number of times of storage of the static image of the object to be observed is equal to or larger than a predetermined number-of-times threshold value. In this case, the number of times of operation of the static-image-acquisition instruction part 13*b* is counted by a number-of-times counter unit (not shown) provided in the processor device 16. Then, in a case where the counted number of times is equal to or larger than a number-of-times threshold value, a mode is automatically switched to the normal mode from the multi-light emission mode as shown in FIG. 12.

Figure 13:
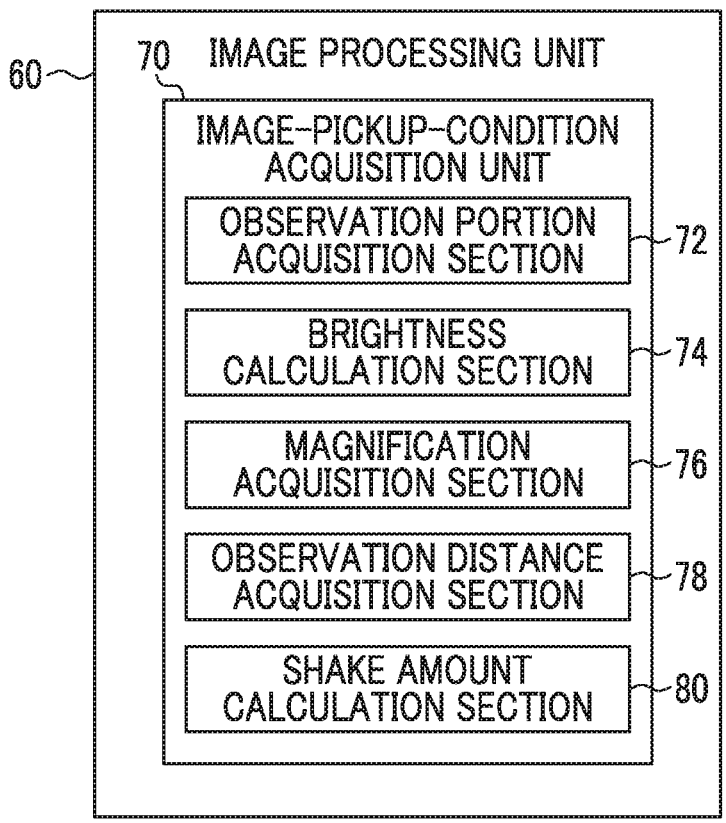
FIG. 13 is a block diagram showing the functions of an image-pickup-condition acquisition unit.

Furthermore, the designated condition is a case where image pickup conditions about the object to be observed are changed. In this case, an image-pickup-condition acquisition unit 70 is provided in the image processing unit 60 of the processor device 16 to acquire the image pickup conditions. As shown in FIG. 13, the image-pickup-condition acquisition unit 70 comprises an observation portion acquisition section 72, a brightness calculation section 74, a magnification acquisition section 76, an observation distance acquisition section 78, and a shake amount calculation section 80.

Figure 14:
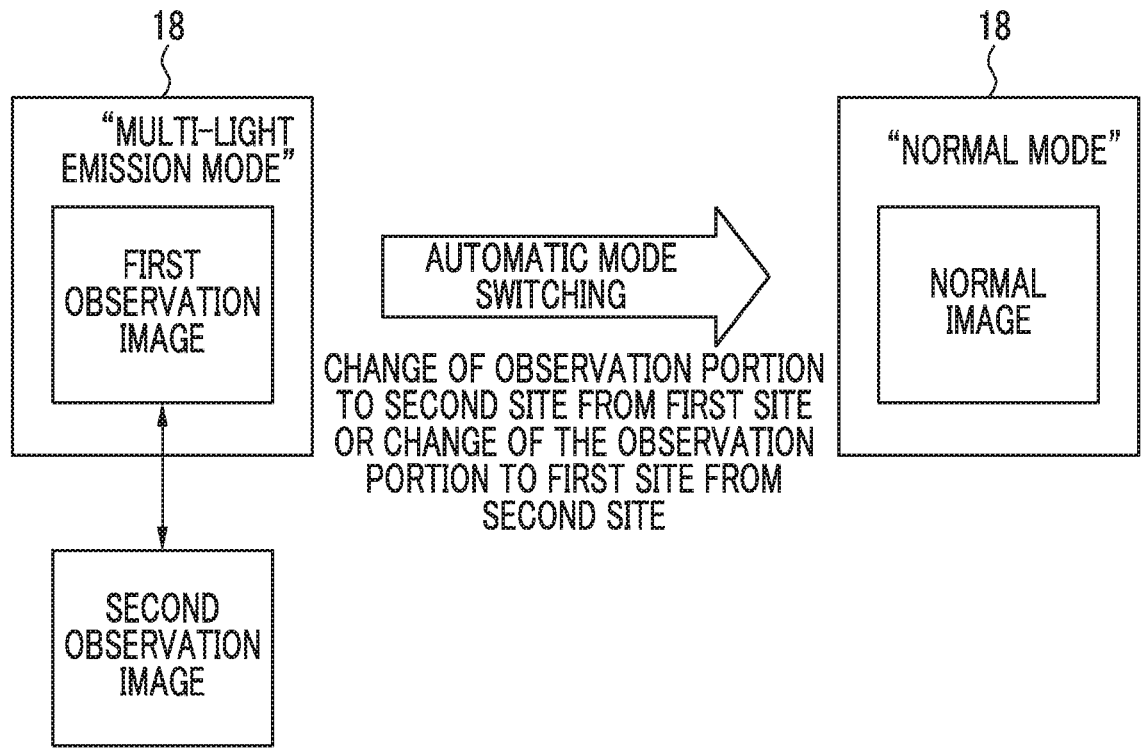
FIG. 14 is a diagram showing that a mode is automatically switched to the normal mode from the multi-light emission mode in a case where an observation portion is changed to a second site from a first site or in a case where an observation portion is changed to the first site from the second site.

In a case where an observation portion, which is one of the image pickup conditions, is changed, for example, in a case where an observation portion of which the image is picked up at present is changed to a second site (for example, "stomach") from a first site (for example, "gullet") or in a case where the observation portion is changed to the first site from the second site as the designated condition, a mode is automatically switched to the normal mode from the multi-light emission mode as shown in FIG. 14. Since it is thought that the distal end part 12*d* of the endoscope is being moved in a case where the observation portion is changed, the object to be observed may not be accurately illuminated with the first illumination light and the second illumination light that are alternately emitted. Accordingly, such a case is not suitable for the multi-light emission mode.

Information about the observation portion is acquired by the observation portion acquisition section 72. The observation portion acquisition section 72 determines the observation portion from the image feature values of the first observation image or the second observation image obtained in the multi-light emission mode. For example, in a case where the brightness of the central portion of the screen is lower than that of a peripheral portion thereof in the first observation image or the second observation image, the observation portion is determined as the "gullet". Further, in a case where the brightness of the central portion of the screen is higher than that of a peripheral portion thereof in the first observation image or the second observation image, the observation portion is determined as the "stomach".

Figure 15:
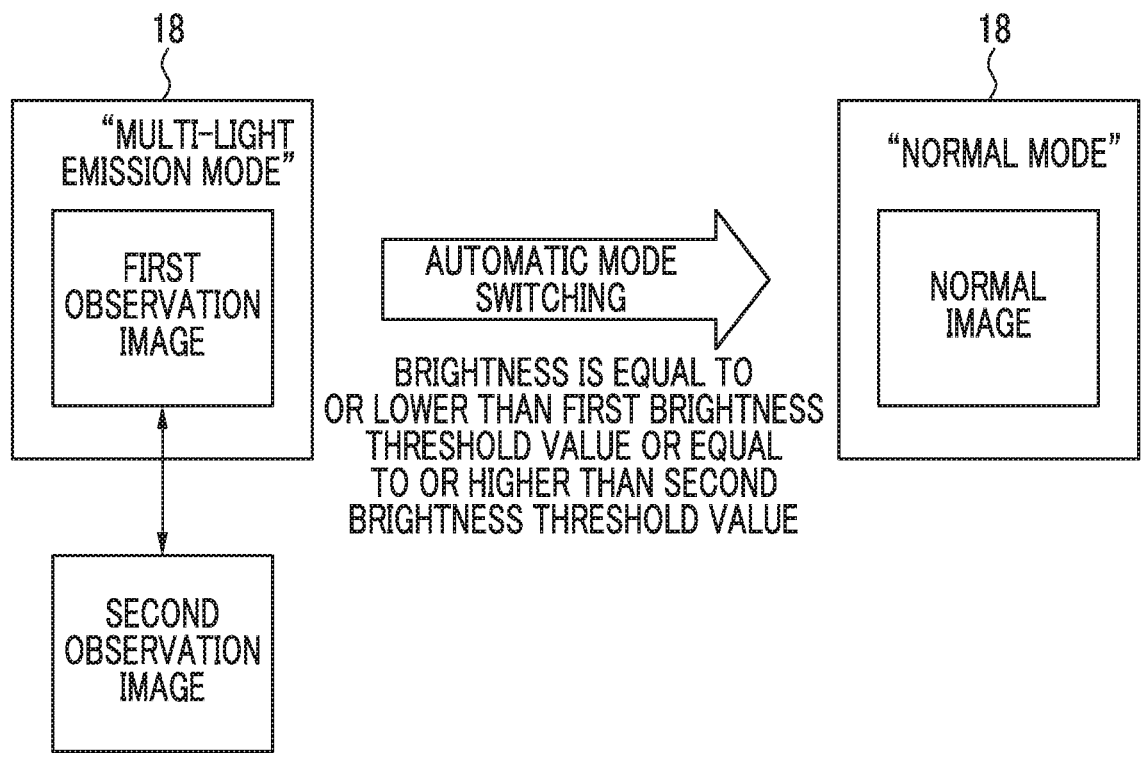
FIG. 15 is a diagram showing that a mode is automatically switched to the normal mode from the multi-light emission mode in a case where brightness is equal to or lower than a first brightness threshold value or brightness is equal to or higher than a second brightness threshold value.

In a case where the brightness of the object to be observed, which is one of the image pickup conditions, is equal to or lower than a first brightness threshold value or is equal to or higher than a second brightness threshold value larger than the first brightness threshold value as the designated condition, a mode is automatically switched to the normal mode from the multi-light emission mode as shown in FIG. 15. In a case where the brightness is equal to or lower than the first brightness threshold value, the entire object to be observed is dark. For this reason, such a case is not suitable for the multi-light emission mode. Likewise, in a case where the brightness is equal to or higher than the second brightness threshold value, the entire object to be observed is extremely bright as in a case where halation occur, and the like. For this reason, such a case is not suitable for the multi-light emission mode. Information about the brightness is acquired by the brightness calculation section 74. The brightness calculation section 74 calculates the average value of pixel values from the first observation image or the second observation image, and calculates brightness from the calculated average value of pixel values. Here, as the average value of pixel values is larger, brightness is higher.

Figure 16:
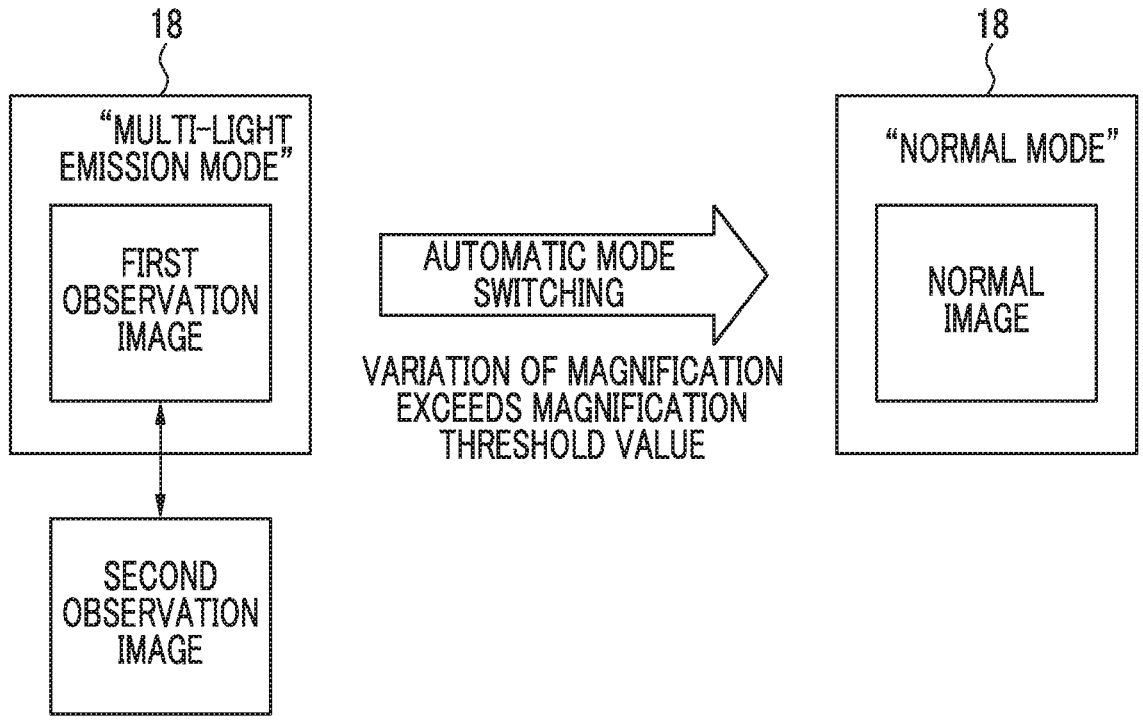
FIG. 16 is a diagram showing that a mode is automatically switched to the normal mode from the multi-light emission mode in a case where the variation of magnification exceeds a magnification threshold value.

In a case where the variation of the magnification of the object to be observed, which is one of the image pickup conditions, exceeds a magnification threshold value as the designated condition, a mode is automatically switched to the normal mode from the multi-light emission mode as shown in FIG. 16. In a case where the magnification of the object to be observed is significantly changed so that the variation of magnification exceeds the magnification threshold value, the distribution of illumination of illumination light on the object to be observed is changed. Accordingly, such a case is often not suitable for the multi-light emission mode. With regard to the magnification of the object, zoom information representing to which magnification the magnification of the object to be observed is set is transmitted to the magnification acquisition section 76 whenever the zoom operation part 13c is operated. The automatic mode-switching unit 69 determines whether or not the variation of magnification exceeds the magnification threshold value with reference to the zoom information acquired by the magnification acquisition section 76.

Figure 17:
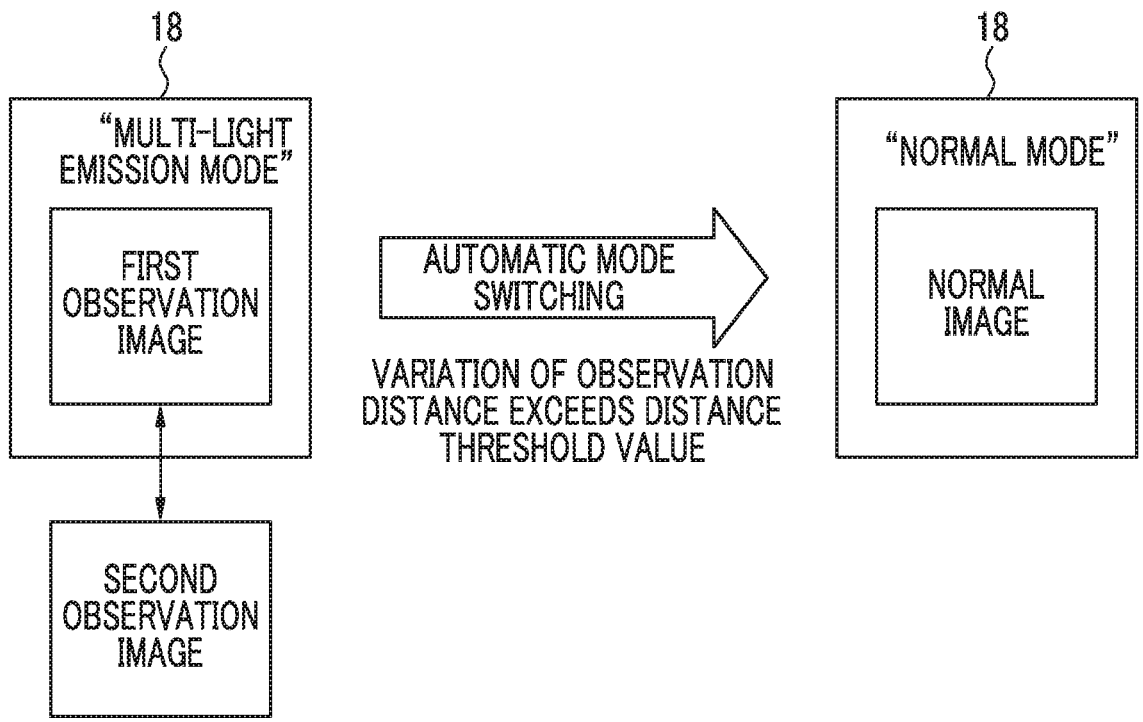
FIG. 17 is a diagram showing that a mode is automatically switched to the normal mode from the multi-light emission mode in a case where the variation of an observation distance exceeds a distance threshold value.

In a case where the variation of an observation distance (a distance between the distal end part 12d of the endoscope and the object to be observed), which is one of the image pickup conditions, exceeds a distance threshold value as the designated condition, a mode is automatically switched to the normal mode from the multi-light emission mode as shown in FIG. 17. As with the magnification of the object to be observed, in a case where the observation distance is significantly changed so that the variation of the observation distance exceeds the distance threshold value, the distribution of illumination of illumination light on the object to be observed is changed. Accordingly, such a case is often not suitable for the multi-light emission mode. With regard to the observation distance, the observation distance acquisition section 78 calculates the average value of pixel values from the first observation image or the second observation image obtained in the multi-light emission mode and obtains an observation distance from the calculated average value of pixel values. Here, as the average value of pixel values is larger, the observation distance is shorter.

Figure 18:
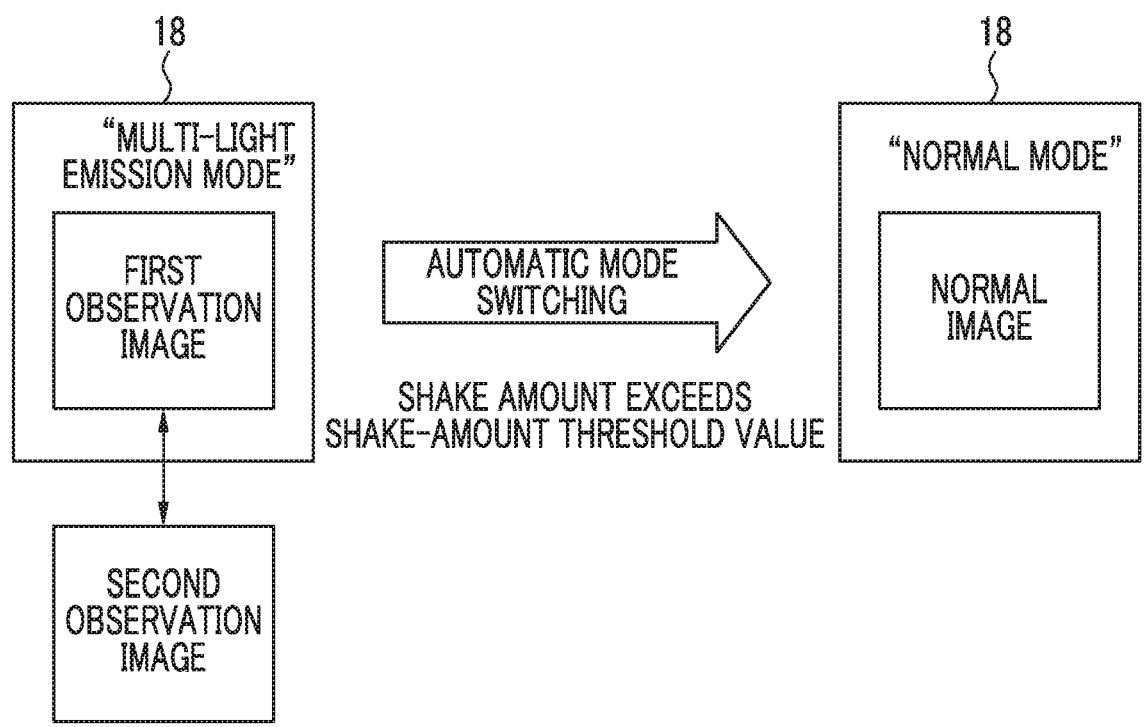
FIG. 18 is a diagram showing that a mode is automatically switched to the normal mode from the multi-light emission mode in a case where a shake amount exceeds a shake-amount threshold value.

In a case where the shake amount of the image, which is one of the image pickup conditions, exceeds a shake-amount threshold value as the designated condition, a mode is automatically switched to the normal mode from the multi-light emission mode as shown in FIG. 18. In a case where the shake amount of the image is large and exceeds the shake-amount threshold value, illumination light may not reliably reach the object to be observed. Accordingly, such a case is often not suitable for the multi-light emission mode. With regard to the shake amount, the shake amount calculation section 80 obtains contrast from the first observation image or the second observation image obtained in the multi-light emission mode and calculates a shake amount from the contrast. As the contrast is lower, the shake amount is larger. A method of calculating the shake amount from the frequency component of the first observation image or the second observation image may be used as a method of calculating the shake amount in addition to a method using contrast (the shake amount is increased as the frequency component becomes a lower frequency component).

Figure 19:
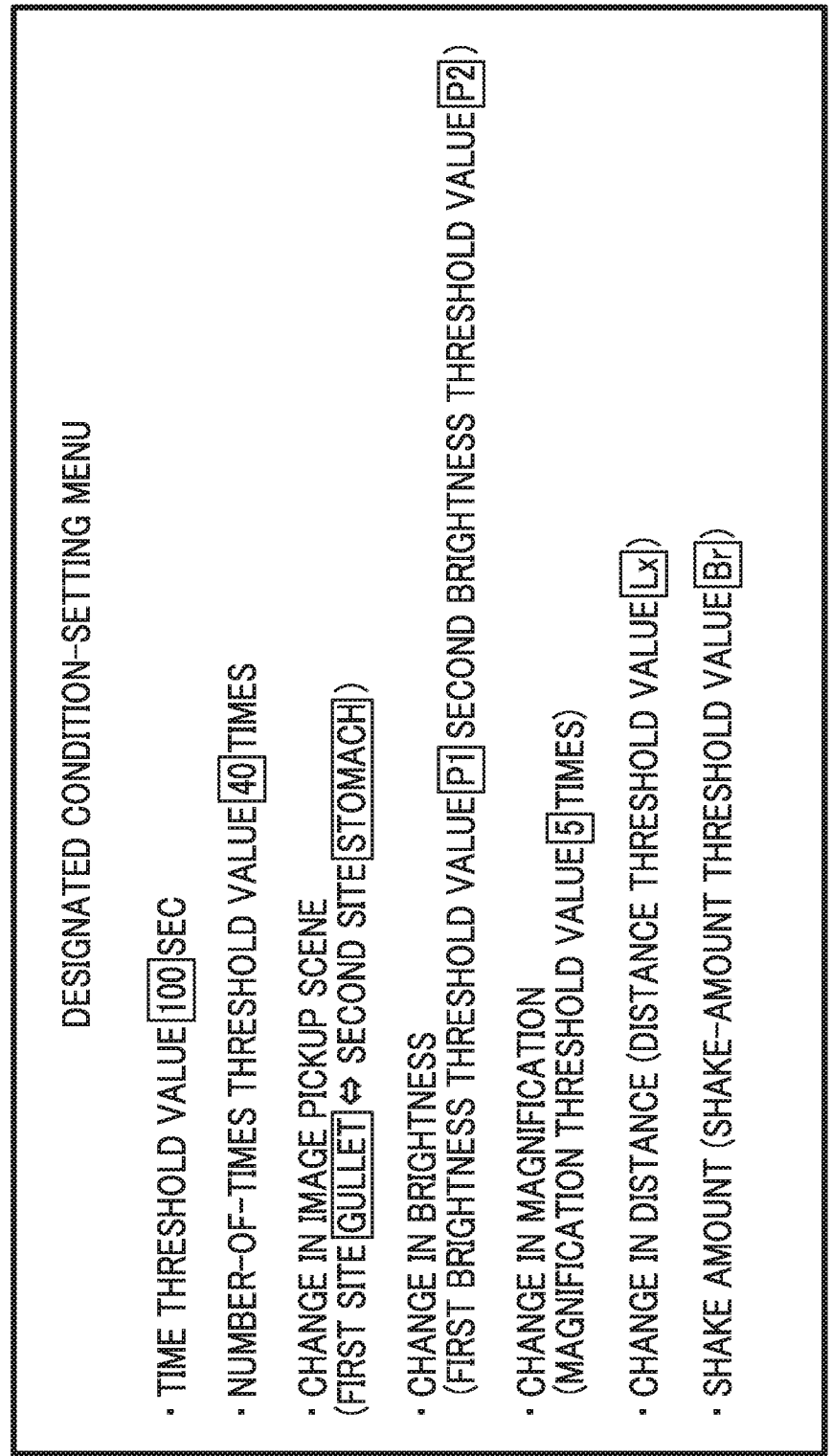
FIG. 19 is an image diagram showing a designated condition-setting menu.

The designated condition that is used for the automatic switching of a mode to the normal mode from the multi-light emission mode can be appropriately set as described above. In this case, a user operates the keyboard 19 to cause the monitor 18 to display a designated condition-setting menu 82 shown in FIG. 19. The "time threshold value" and the "number-of-times threshold value" can be set in the designated condition-setting menu 82. In a case where the "time threshold value" is set to "100 sec." in the designated condition-setting menu 82, a mode is automatically switched to the normal mode from the multi-light emission mode at the point of time when the use time of the multi-light emission mode reaches "100 sec.". Further, in a case where the "number-of-times threshold value" is set to "40 times" in the designated condition-setting menu 82, a mode is automatically switched to the normal mode from the multi-light emission mode at the point of time when the number of times of operation of the static-image-acquisition instruction part 13b reaches "40 times".

Furthermore, the "first site" and the "second site" can be set in the designated condition-setting menu 82. In a case where the "first site" is set to the "gullet" and the "second site" is set to the "stomach" and the observation portion is changed to the "stomach" from the "gullet" or a case where the observation portion is changed to the "gullet" from the "stomach", a mode is automatically switched to the normal mode from the multi-light emission mode. Moreover, the "first brightness threshold value" and the "second brightness threshold value" can be set in the designated condition-setting menu 82. In a case where the "first brightness threshold value" is set to P1 and the "second brightness threshold value" is set to P2 (>P1) and the brightness of the object to be observed is equal to or lower than P1 or is equal to or higher than P2, a mode is automatically switched to the normal mode from the multi-light emission mode.

Further, the "magnification threshold value" can be set in the designated condition-setting menu 82. In a case where the "magnification threshold value" is set to "5 times", a mode is automatically switched to the normal mode from the multi-light emission mode at the point of time when the variation of magnification of the object to be observed exceeds "5 times". Furthermore, the "distance threshold value" can be set in the designated condition-setting menu 82. In a case where the "distance threshold value" is set to Lx and the variation of the observation distance exceeds Lx, a mode is automatically switched to the normal mode from the multi-light emission mode. Moreover, the "shake-amount threshold value" can be set in the designated condition-setting menu 82. In a case where the "shake-amount threshold value" is set to Br and the shake amount is exceeds Br, a mode is automatically switched to the normal mode from the multi-light emission mode.

Figure 20:
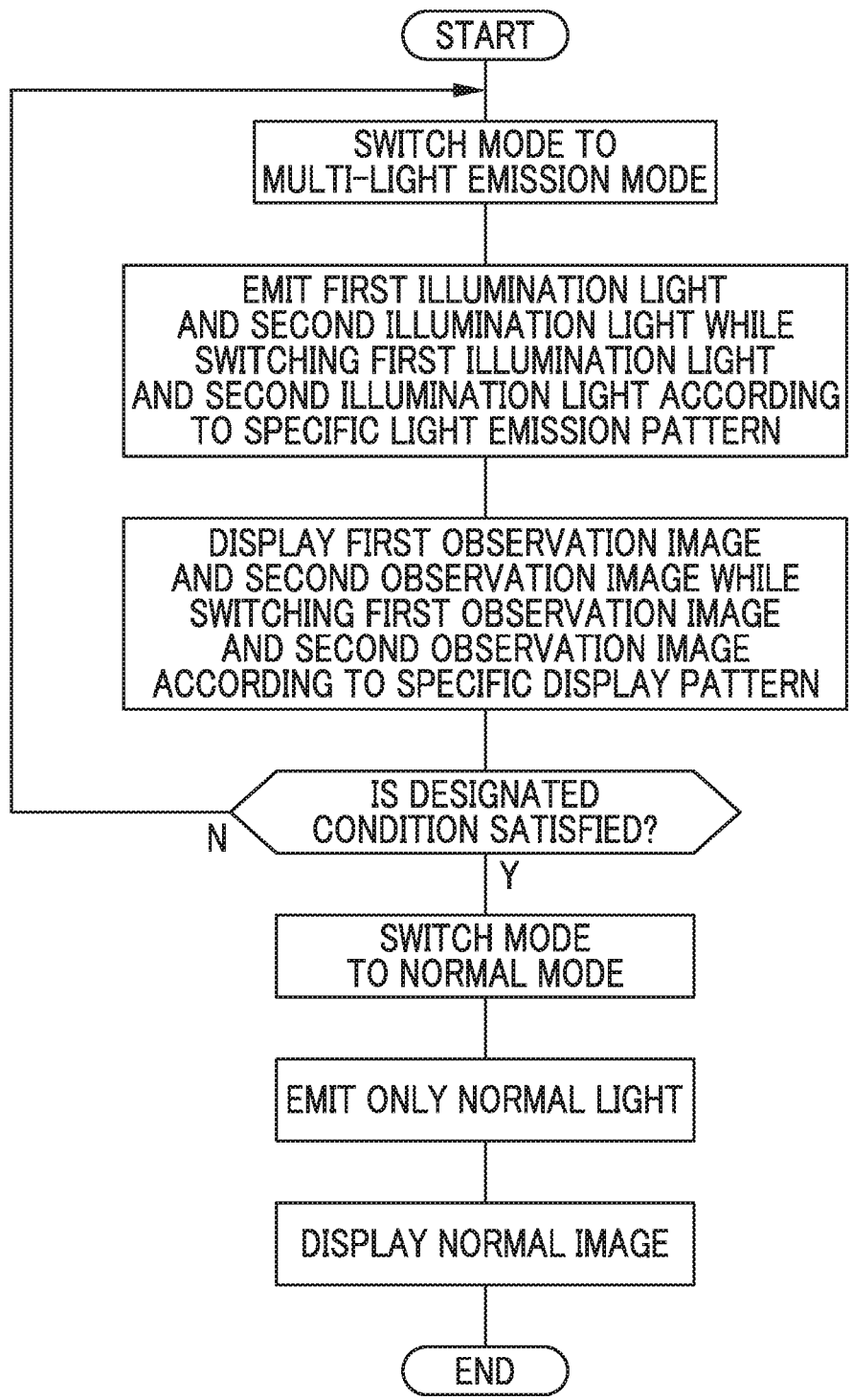
FIG. 20 is a flowchart showing a series of flow where a mode is automatically switched to the normal mode from the multi-light emission mode.

Next, a series of flow where a mode is automatically switched to the normal mode from the multi-light emission mode will be described with reference to a flowchart shown in FIG. 20. In the multi-light emission mode, the first illumination light and the second illumination light are emitted while being switched according to a specific light emission pattern (in this embodiment, at an interval of two frames). Further, the first observation image obtained from the image pickup of an object to be observed illuminated with the first illumination light and the second observation image obtained from the image pickup of the object to be observed illuminated with the second illumination light are displayed on the monitor 18 while being switched according to a specific display pattern (in this embodiment, at an interval of two frames).

Furthermore, in a case where a designated condition predetermined by a user is satisfied, a mode is automatically switched to the normal mode from the multi-light emission mode. The designated condition includes a case where the use time of the multi-light emission mode exceeds the time threshold value or a case where the number of times of storage of a static image exceeds the number-of-times threshold value. Moreover, the designated condition includes a case where the image pickup conditions about the object to be observed are changed. In a case where a mode is automatically switched to the normal mode, the switching and emission of the first illumination light and the second illumination light are stopped. According to this, the switching and display of the first and second observation images are also stopped. Then, the normal light is emitted and the normal image obtained from the image pickup of the object to be observed illuminated with the normal light is displayed on the monitor 18.

In the embodiment, the first illumination light and the second illumination light have been emitted while being switched according to the specific light emission pattern, and the first observation image corresponding to the first illumination light and the second observation image corresponding to the second illumination light have been displayed on the monitor 18 while being switched according to the specific display pattern. However, three or more kinds of illumination light having wavelength ranges different from each other may be emitted while being switched according to a specific light emission pattern, and three or more kinds of observation images corresponding to the three or more kinds of illumination light may be displayed on the monitor 18 while being switched according to a specific display pattern.

The hardware structures of the processing units, which are included in the processor device 16 in the embodiment, such as the image acquisition unit 53, the DSP 56, the noise removing unit 58, the image processing unit 60, the parameter switching unit 62, the central control unit 68, and the automatic mode-switching unit 69, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope system
12: endoscope
12a: insertion part
12b: operation part
12c: bendable part
12d: distal end part
12e: angle knobs
13b: static-image-acquisition instruction part
13c: zoom operation part
14: light source device
16: processor device
18: monitor
19: keyboard
20: light source unit
20a: V-LED (violet light emitting diode)
20b: B-LED (blue light emitting diode)
20c: G-LED (green light emitting diode)
20d: R-LED (red light emitting diode)
21: light source control unit
23: optical path-combination unit
30a: illumination optical system
30b: image pickup optical system
41: light guide
45: illumination lens
46: objective lens
47: zoom lens
47a: zoom drive unit
48: image pickup sensor
50: CDS/AGC circuit
53: image acquisition unit
56: digital signal processor (DSP)
58: noise removing unit
60: image processing unit
62: parameter switching unit
63: static image-storage unit
66: display control unit
68: central control unit
69: automatic mode-switching unit
70: image-pickup-condition acquisition unit
72: observation portion acquisition section
74: brightness calculation section
76: magnification acquisition section
78: observation distance acquisition section
80: shake amount calculation section
82: designated condition-setting menu

What is claimed is:
1. An endoscope system comprising:
a plurality of semiconductor light sources that emit light having wavelength ranges different from each other;
a light source controller that controls the plurality of semiconductor light sources and performs control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern;
a processor configured to function as:
a display control unit that performs control to display a specific observation image, which is obtained from image pickup of an object to be observed illuminated with the specific illumination light, on a display in the mono-light emission mode and performs control to display a plurality of observation images, which include a first observation image obtained from image pickup of the object to be observed illuminated with the first illumination light and a second observation image obtained from image pickup of the object to be observed illuminated with the second illumination light, on the display while switching the plurality of observation images according to a specific display pattern in the multi-light emission mode; and an automatic mode-switching unit that automatically switches a mode to the mono-light emission mode from the multi-light emission mode in a case where a designated condition set in advance by a user is satisfied, wherein the designated condition is that a use time of the multi-light emission mode is equal to or longer than a time threshold value.

2. An endoscope system comprising:

a plurality of semiconductor light sources that emit light having wavelength ranges different from each other;

a light source controller that controls the plurality of semiconductor light sources and performs control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern;

a processor configured to function as:
    a display control unit that performs control to display a specific observation image, which is obtained from image pickup of an object to be observed illuminated with the specific illumination light, on a display in the mono-light emission mode and performs control to display a plurality of observation images, which include a first observation image obtained from image pickup of the object to be observed illuminated with the first illumination light and a second observation image obtained from image pickup of the object to be observed illuminated with the second illumination light, on the display while switching the plurality of observation images according to a specific display pattern in the multi-light emission mode; and
    an automatic mode-switching unit that automatically switches a mode to the mono-light emission mode from the multi-light emission mode in a case where a designated condition set in advance by a user is satisfied, wherein the designated condition is that the number of times of storage of a static image of the object to be observed is equal to or larger than a number-of-times threshold value.

3. An endoscope system comprising:

a plurality of semiconductor light sources that emit light having wavelength ranges different from each other;

a light source controller that controls the plurality of semiconductor light sources and performs control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern;

a processor configured to function as:
    a display control unit that performs control to display a specific observation image, which is obtained from image pickup of an object to be observed illuminated with the specific illumination light, on a display in the mono-light emission mode and performs control to display a plurality of observation images, which include a first observation image obtained from image pickup of the object to be observed illuminated with the first illumination light and a second observation image obtained from image pickup of the object to be observed illuminated with the second illumination light, on the display while switching the plurality of observation images according to a specific display pattern in the multi-light emission mode; and
    an automatic mode-switching unit that automatically switches a mode to the mono-light emission mode from the multi-light emission mode in a case where a designated condition set in advance by a user is satisfied, wherein the designated condition is a case where an image pickup condition about the object to be observed is changed.

4. The endoscope system according to claim 3, wherein the object to be observed includes a first site and a second site different from the first site, and the designated condition is a case where the object to be observed is changed to the second site from the first site or a case where the object to be observed is changed to the first site from the second site.

5. The endoscope system according to claim 4, wherein the first site is a gullet and the second site is a stomach.

6. The endoscope system according to claim 3, wherein the designated condition is a case where brightness of the object to be observed is equal to or lower than a first brightness threshold value or is equal to or higher than a second brightness threshold value larger than the first brightness threshold value.

7. The endoscope system according to claim 3, further comprising:

a magnification change device that is used to change magnification of the object to be observed, wherein the designated condition is a case where a variation of magnification of the object to be observed exceeds a magnification threshold value.

8. The endoscope system according to claim 3, wherein the processor is further configured to function as an observation distance acquisition section that acquires an observation distance indicating a distance to the object to be observed, and wherein the designated condition is a case where a variation of the observation distance exceeds a distance threshold value.

9. The endoscope system according to claim 3, wherein the processor is further configured to function as a shake amount calculation section that calculates a shake amount of the observation image, and wherein the designated condition is a case where the shake amount exceeds a shake-amount threshold value.

10. A method of operating an endoscope system, the method comprising:

a light source control step of causing a light source controller, which controls a plurality of semiconductor light sources emitting light having wavelength ranges different from each other, to perform control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern;

a display control step of causing a processor to perform control to display a specific observation image, which is obtained from image pickup of an object to be observed illuminated with the specific illumination light, on a display in the mono-light emission mode and to perform control to display a plurality of observation images, which include a first observation image obtained from image pickup of the object to be observed illuminated with the first illumination light and a second observation image obtained from image pickup of the object to be observed illuminated with the second illumination light, on the display while switching the plurality of observation images according to a specific display pattern in the multi-light emission mode; and a mode switching step of causing the processor to automatically switch a mode to the mono-light emission mode from the multi-light emission mode in a case where a designated condition set in advance by a user is satisfied, wherein the designated condition is that a use time of the multi-light emission mode is equal to or longer than a time threshold value.

11. A method of operating an endoscope system, the method comprising:

a light source control step of causing a light source controller, which controls a plurality of semiconductor light sources emitting light having wavelength ranges different from each other, to perform control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern;

a display control step of causing a processor to perform control to display a specific observation image, which is obtained from image pickup of an object to be observed illuminated with the specific illumination light, on a display in the mono-light emission mode and to perform control to display a plurality of observation images, which include a first observation image obtained from image pickup of the object to be observed illuminated with the first illumination light and a second observation image obtained from image pickup of the object to be observed illuminated with the second illumination light, on the display while switching the plurality of observation images according to a specific display pattern in the multi-light emission mode; and a mode switching step of causing the processor to automatically switch a mode to the mono-light emission mode from the multi-light emission mode in a case where a designated condition set in advance by a user is satisfied, wherein the designated condition is that the number of times of storage of a static image of the object to be observed is equal to or larger than a number-of-times threshold value.

12. A method of operating an endoscope system, the method comprising:

a light source control step of causing a light source controller, which controls a plurality of semiconductor light sources emitting light having wavelength ranges different from each other, to perform control for a mono-light emission mode where only specific illumination light having a specific light emission ratio is emitted and control for a multi-light emission mode where a plurality of kinds of illumination light, which include first illumination light having a first light emission ratio and second illumination light having a second light emission ratio different from the first light emission ratio, are emitted while being switched according to a specific light emission pattern;

a display control step of causing a processor to perform control to display a specific observation image, which is obtained from image pickup of an object to be observed illuminated with the specific illumination light, on a display in the mono-light emission mode and to perform control to display a plurality of observation images, which include a first observation image obtained from image pickup of the object to be observed illuminated with the first illumination light and a second observation image obtained from image pickup of the object to be observed illuminated with the second illumination light, on the display while switching the plurality of observation images according to a specific display pattern in the multi-light emission mode; and a mode switching step of causing the processor to automatically switch a mode to the mono-light emission mode from the multi-light emission mode in a case where a designated condition set in advance by a user is satisfied, wherein the designated condition is a case where an image pickup condition about the object to be observed is changed.

* * * * *